United States Patent
Tanaka et al.

(10) Patent No.: US 9,730,589 B2
(45) Date of Patent: Aug. 15, 2017

(54) EXAMINED-PORTION INFORMATION ACQUISITION APPARATUS

(71) Applicant: CANON KABUSHIKI KAISHA, Tokyo (JP)

(72) Inventors: Takatoshi Tanaka, Tokyo (JP); Kenichi Nagae, Yokohama (JP); Robert A Kruger, Oriental, NC (US)

(73) Assignee: CANON KABUSHIKI KAISHA, Tokyo (JP)

( * ) Notice: Subject to any disclaimer, the term of this patent is extended or adjusted under 35 U.S.C. 154(b) by 269 days.

(21) Appl. No.: 14/527,434

(22) Filed: Oct. 29, 2014

(65) Prior Publication Data

US 2015/0114125 A1    Apr. 30, 2015

Related U.S. Application Data

(60) Provisional application No. 61/898,075, filed on Oct. 31, 2013.

(51) Int. Cl.
*A61B 5/00* (2006.01)

(52) U.S. Cl.
CPC .......... *A61B 5/0095* (2013.01); *A61B 5/4312* (2013.01); *A61B 5/708* (2013.01); *A61B 2560/04* (2013.01)

(58) Field of Classification Search
CPC ..... A61B 5/0095; A61B 5/4312; A61B 5/708; A61B 2560/04
USPC ......................................................... 73/632
See application file for complete search history.

(56) References Cited

U.S. PATENT DOCUMENTS

| | | | | |
|---|---|---|---|---|
| 7,864,307 B2* | 1/2011 | Fukutani | ............... | A61B 5/0073 356/73 |
| 8,876,717 B2* | 11/2014 | Tokita | .................. | A61B 5/0091 600/437 |
| 8,977,337 B2* | 3/2015 | Oyama | ................ | A61B 5/0095 600/407 |
| 8,991,261 B2* | 3/2015 | Asao | ..................... | A61B 5/0059 73/655 |

(Continued)

FOREIGN PATENT DOCUMENTS

JP    4341987 B2    10/2009

*Primary Examiner* — J M Saint Surin
(74) *Attorney, Agent, or Firm* — Canon U.S.A., Inc. IP Division (57) ABSTRACT

One aspect of the present invention relates to an examined-portion information acquisition apparatus including two examined-portion holding members each configured to hold one of two examined portions, a receiver configured to receive an acoustic wave, and a moving system configured to move the receiver from a position at which the receiver receives an acoustic wave from one examined portion held by one examined-portion holding member among the two examined-portion holding members to a position at which the receiver receives an acoustic wave from another examined portion held by the other examined-portion holding member, wherein the receiver includes a plurality of transducers configured to receive an acoustic wave, and a supporting member on which the plurality of transducers are arranged, and the plurality of transducers are arranged on the supporting member such that directivity axes of some transducers among the plurality of transducers converge.

22 Claims, 7 Drawing Sheets

(56) References Cited

U.S. PATENT DOCUMENTS

| | | | |
|---|---|---|---|
| 8,997,571 B2* | 4/2015 | Someda | A61B 5/0095 |
| | | | 73/579 |
| 9,086,365 B2* | 7/2015 | Wang | A61B 5/0095 |
| 9,128,032 B2* | 9/2015 | Carson | A61B 5/0059 |
| 9,173,633 B2* | 11/2015 | Sudo | A61B 5/0095 |
| 9,202,124 B2* | 12/2015 | Wanda | A61B 5/0095 |
| 9,339,254 B2* | 5/2016 | Wanda | A61B 5/14542 |
| 9,351,705 B2* | 5/2016 | Wang | A61B 5/0062 |
| 9,370,307 B2* | 6/2016 | Wada | A61B 5/0095 |
| 9,417,179 B2* | 8/2016 | Wada | A61B 5/0095 |
| 9,439,571 B2* | 9/2016 | Wang | A61B 5/0095 |
| 2013/0167648 A1* | 7/2013 | Tokita | A61B 5/0095 |
| | | | 73/655 |
| 2015/0031998 A1* | 1/2015 | Kyono | A61B 8/4281 |
| | | | 600/437 |
| 2015/0141795 A1* | 5/2015 | Kim | A61B 8/42 |
| | | | 600/407 |

* cited by examiner

1. MEASURE LEFT BREAST

2. MOVE TOWARD −Z DIRECTION

3. MOVE TOWARD +X DIRECTION

4. MOVE TOWARD +Z DIRECTION

5. MEASURE RIGHT BREAST

FIG. 8

EXAMINED-PORTION INFORMATION ACQUISITION APPARATUS

BACKGROUND OF THE INVENTION

Field of the Invention

The present invention relates to examined-portion information acquisition apparatuses. Specifically, the present invention relates to, for example, photoacoustic apparatuses for measuring an acoustic wave produced by the photoacoustic effect. As photoacoustic apparatuses, there are photoacoustic apparatuses for use in observation of a chest portion of a living body, etc.

Description of the Related Art

Recently, the development of photoacoustic tomography (PAT) diagnosis apparatuses that utilize the photoacoustic effect has been promoted. These apparatuses radiate illumination light (near-infrared light) from a pulsed Nd:YAG laser light source onto a target object; receive, using a two-dimensional or three-dimensional array of transducers, an acoustic wave produced by the photoacoustic effect inside the target object upon irradiation, and generate and display an image. A specific procedure of a photoacoustic-effect-based imaging method is as follows:

(1) The two-dimensional array of transducers is positioned with respect to the surface of an examined object, and single-pulse electromagnetic energy is radiated onto an examined portion;

(2) Signals received by the individual transducers are sampled and stored from when the electromagnetic energy has been radiated;

(3) For each point Ps inside the examined portion to be visualized, delay times taken by an acoustic wave to reach positions Pt of the individual transducers i from the point Ps are calculated, and signals of the individual transducers obtained at timings corresponding to the calculated delay times are added together, and the resulting sum is used as a pixel value for the point Ps; and (4) Step (3) is repeated for each point Ps to be imaged.

As an example of photoacoustic apparatuses according to the related art, Japanese Patent No. 4341987 discloses an apparatus that performs a photoacoustic measurement by causing a receiver including spirally arranged transducers to perform a scan in a circular motion.

In order to receive acoustic waves produced at two examined portions (e.g., right and left breasts) by using the apparatus disclosed in Japanese Patent No. 4341987, an examined person needs to change the examined portion. For example, in the case where acoustic waves produced at the right and left breasts are received, a motion to change the breast while in a prone position imposes a physical load on the examined person, and increases the time required for reception.

SUMMARY OF THE INVENTION

One aspect of the present invention relates to an examined-portion information acquisition apparatus including two examined-portion holding members each configured to hold an examined portion; a receiver configured to receive an acoustic wave; and a moving system configured to move the receiver from a position at which the receiver receives an acoustic wave from one examined portion held by one examined-portion holding member among the two examined-portion holding members to a position at which the receiver receives an acoustic wave from another examined portion held by the other examined-portion holding member, wherein the receiver includes a plurality of transducers each configured to receive an acoustic wave, and a supporting member on which the plurality of transducers are arranged, and the plurality of transducers are arranged on the supporting member such that directivity axes of some transducers among the plurality of transducers converge.

In addition, another aspect of the present invention relates to an examined-portion information acquisition apparatus including an examined-object supporting member including two openings; a receiver configured to receive an acoustic wave; and a moving system configured to move the receiver from a position at which the receiver receives an acoustic wave from one examined portion inserted into one opening among the two openings to a position at which the receiver receives an acoustic wave from another examined portion inserted into the other opening, wherein the receiver includes a plurality of transducers each configured to receive an acoustic wave, and a supporting member on which the plurality of transducers are arranged, and the plurality of transducers are arranged on the supporting member such that directivity axes of some transducers among the plurality of transducers converge.

Further features of the present invention will become apparent from the following description of exemplary embodiments with reference to the attached drawings.

DESCRIPTION OF THE EMBODIMENTS

Exemplary embodiments of the present invention will be described below with reference to the drawings. It should be noted that the present invention is not limited to these exemplary embodiments unless embodiments deviate from the scope of this invention.

It should be also noted that a scan performed by a receiver encompasses not only movement of the receiver performed while receiving an acoustic wave but also movement of the receiver performed without receiving an acoustic wave. Herein, the term "measurement" refers to a process in which the receiver receives an acoustic wave produced inside an examined object.

In addition, herein, examples of examined-object information include a distribution of initial sound pressures of acoustic waves, a distribution of optical energy absorption densities, a distribution of absorption coefficients, and a distribution of concentrations of materials that form the examined object. The concentrations of materials include, for example, a degree of oxygen saturation, an oxyhemoglobin concentration, a deoxyhemoglobin concentration, and a total hemoglobin concentration. The total hemoglobin concentration is the sum of the concentrations of oxyhemoglobin and deoxyhemoglobin.

First Embodiment

Figure 1:
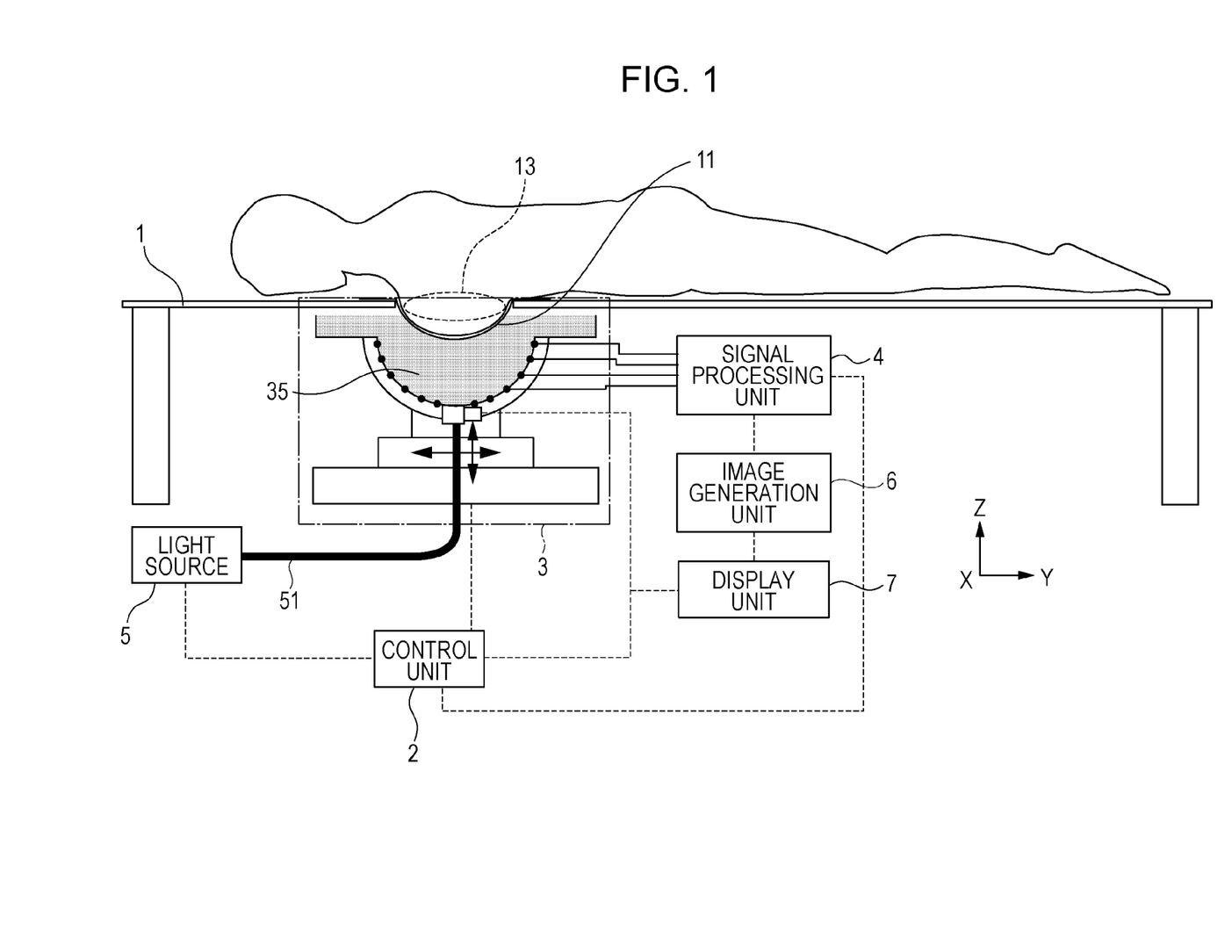
FIG. 1 is a conceptual diagram of an examined-portion information acquisition apparatus.

FIG. 1 is a conceptual diagram of an examined-portion information acquisition apparatus according to a first embodiment of the present invention. In this embodiment, an examined-portion information acquisition apparatus that receives acoustic waves from breasts serving as examined portions will be described by way of example. An examined person (examined object) takes a prone position on a bed 1, which is an examined-object supporting member, to let the breasts droop and bring the breasts into contact with holding members 11 (examined-portion holding members).

A space between the holding member 11 and the breast is filled with a matching agent (not illustrated) to allow ultrasonic waves to more easily transmit therethrough. Examples of the matching agent include water, a gel, etc. The examined-portion information acquisition apparatus according to this embodiment of the present invention includes, for each of the right and left breasts, the holding member 11 which is provided in different shapes and in a plurality of sizes depending on the size of the breast. By permitting installation of the holding member 11 provided in a plurality of shapes and sizes, creation of a gap between the breast and the holding member 11 is suppressed. The examined-portion information acquisition apparatus according to this embodiment consecutively receives acoustic waves from the right and left breasts. At this time, an operator performs an input regarding only an acoustic wave reception region for one of the breasts.

A signal processing unit 4 performs analog-to-digital (A/D) conversion to generate digital data (digitized reception signal). An image generation unit 6 generates a two-dimensional or three-dimensional photoacoustic image on the basis of the reception signal. A display unit 7 displays the generated photoacoustic image and an image captured with a camera 33.

Note that the image generation unit 6 is capable of acquiring examined-object information by performing processing on the reception signal on the basis of an image reconstruction algorithm. Examples of the image reconstruction algorithm used for acquiring examined-object information include time-domain or Fourier-domain reverse projection which is generally used in tomographic technology. In the case where a long time is permitted for reconstruction, an image reconstruction method such as an inverse problem analysis based on iterated processing may be used.

Herein, the term "processing unit" is a concept including the signal processing unit 4 and the image generation unit 6. A computing unit of the signal processing unit 4 or the image generation unit 6 typically includes elements such as a central processing unit (CPU), a graphics processing unit (GPU), and an A/D converter, or a circuit such as a field programmable gate array (FPGA) or an application-specific integrated circuit (ASIC). The computing unit may be constituted by one element or circuit, or by a plurality of elements or circuits. Also, each process may be executed by any of the element and the circuit.

The holding member 11 (examined-portion holding member) is configured to hold an examined portion. In this embodiment, the holding member 11 has a bowl-like shape so that the breast is well held therein. The holding member 11 need not have a complete spherical surface and it is sufficient that the holding member 11 has a shape in which the breast and the axillary region fit. Preferably, the holding member 11 is provided in a different shape for each of the right and left breasts and in a plurality of sizes depending on the size of the breast.

Preferably, the holding member 11 is formed of a member that is thin (0.1 to 0.5 mm) to allow ultrasonic waves to easily transmit therethrough, that is transparent to allow light to transmit therethrough, and that is strong enough to support the weight of the examined person. PET (polyethylene terephthalate) is suitable as a material of the holding member 11 having such properties. Alternatively, the holding member 11 may be formed of a material deformable into the shape of an examined portion. For example, as the holding member 11, a sheet-like member formed of a material having a Young's modulus smaller than a typical Young's modulus of the breast may be employed.

A light source 5 supplies optical energy to an examined portion (e.g., breast) of an examined object so as to cause the examined portion to produce an acoustic wave. In the case where the examined object is a living body, the light source 5 radiates light of a specific wavelength which is absorbed by a specific constituent among constituents of a living body. For example, the light source 5 radiates near-infrared light onto the examined portion. The light source 5 may be integrally provided in the examined-portion information acquisition apparatus according to this embodiment or may be provided separately as an independent device.

The light source 5 is preferably a pulsed light source which is capable of producing pulsed light on the order of several to several hundreds of nanoseconds as radiation light. Specifically, a pulse width of approximately 10 to 100 nanoseconds is used in order to efficiently produce an acoustic wave. The light source 5 is preferably a laser because a high output is obtained with a laser; however, a light-emitting diode or the like may be used instead of a laser. Various types of laser such as a solid-state laser, a gas laser, a fiber laser, a dye laser, and a semiconductor laser can be used as the laser. Timings, a waveform, an intensity, etc. of radiation are controlled by a light-source control unit (not illustrated). In this embodiment of the present invention, a wavelength used by the light source 5 is preferably a wavelength at which light propagates to inside of the breast. Specifically, the wavelength is longer than or equal to 500 nm and shorter than or equal to 1200 nm.

Figure 2:
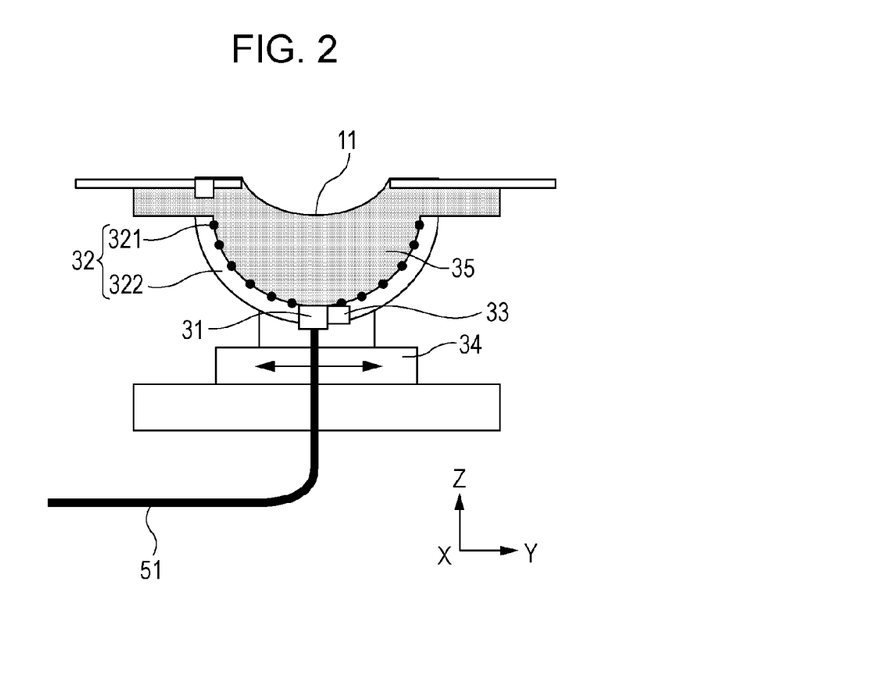
FIG. 2 is a conceptual diagram of a reception unit.

FIG. 2 is a conceptual diagram of a reception unit 3 according to this embodiment of the present invention. The reception unit 3 includes a light radiation unit 31 configured to irradiate the breast with laser light supplied from the light source 5 (not illustrated) and led through a light guide 51; a receiver 32 configured to receive an acoustic wave (ultrasonic wave) produced at the breast; and the camera 33 used to observe the holding state of the breast. In addition, the reception unit 3 further includes a moving system 34 configured to move the light radiation unit 31, the receiver 32, the camera 33, or the like. The light radiation unit 31 is arranged, for example, at a position where the light radiation unit 31 opposes the breast and radiates laser light onto the breast. An acoustic wave produced by thermal expansion is received by the receiver 32. A space between the receiver 32 and the holding member 11 is filled with a matching agent 35. The receiver 32 includes a matching-agent container that is filled with the matching agent 35. Water or the like having an acoustic impedance that is closer to that of the human body than air does is used as the matching agent 35.

The receiver 32 includes a plurality of transducers 321 each configured to receive an acoustic wave, and a supporting member 322 (transducer supporting member) on which the plurality of transducers 321 are arranged. Typically, the reception sensitivity is the highest in the normal direction of the reception surface of the transducer, and the reception sensitivity lowers as the incident angle increases. Herein, an axis along the direction in which the transducer has the highest reception sensitivity is referred to as a "directivity axis". The plurality of transducers are arranged on the supporting member such that a direction in which at least one transducer among the plurality of transducers has a high reception sensitivity is different from a direction in which another transducer among the plurality of transducers has a high reception sensitivity and the direction in which the at least one transducer has a high reception sensitivity points toward a certain region. Here, the certain region is a region set such that in the case where directions in which the plurality of transducers have high reception sensitivities point toward the certain region, the plurality of transducers can receive an acoustic wave produced in the certain region at a higher sensitivity than in the case where the high reception-sensitivity directions are in parallel with one another. In this embodiment, the plurality of transducers 321 each configured to receive a photoacoustic wave are arranged on the supporting member 322 such that directivity axes of at least some of the plurality of transducers 321 converge.

With this configuration, a resolution of an image regarding the certain region which is created on the basis of an acoustic wave received from the certain region can be made higher than that of the case where directions in which the plurality of transducers have high reception sensitivities are in parallel with one another.

Accordingly, the plurality of transducers may at least include a first transducer and a second transducer that are arranged on the supporting member such that directions in which the first and second transducers have high reception sensitivities are different from each other (are not in parallel with each other) and point toward a certain region.

Alternatively, the plurality of transducers may include a first transducer and a second transducer that are arranged on the supporting member such that directions in which the first and second transducers have the highest reception sensitivities are different from each other and point toward a certain region. That is, the plurality of transducers may be arranged on the supporting member such that a direction in which at least one transducer among the plurality of transducers has the highest reception sensitivity is different from a direction in which another transducer among the plurality of transducers has the highest reception sensitivity and the direction in which the at least one transducer has the highest reception sensitivity points toward a certain region. Here, the certain region is a region set such that in the case where directions in which the plurality of transducers have the highest reception sensitivities point toward the certain region, the plurality of transducers can receive an acoustic wave produced in the certain region at a higher sensitivity than in the case where the highest reception-sensitivity directions are in parallel with one another.

This arrangement of the plurality of transducers can increase a reception sensitivity of the receiver 32 to an acoustic wave propagating from the certain region. In addition, this arrangement can make a resolution of an image regarding the certain region which is created on the basis of an acoustic wave received from the certain region higher than that of the case where directions in which the plurality of transducers have the highest reception sensitivities are in parallel with one another.

By causing directions in which the reception sensitivities of the plurality of transducers become higher than a certain level to point toward a certain region, the resolution of an image corresponding to the region can be increased. Herein, a region for which reception can be performed at a high sensitivity in this manner is referred to as a high-sensitivity region. The high-sensitivity region consequently becomes a high-resolution region. In addition, herein, the high-resolution region refers to a region having a resolution ranging from the highest resolution to a half the highest resolution. Specifically, a diameter r in Expression (1) below represents a diameter of the high-resolution region.

$$r = \frac{r_0}{\phi_d} \cdot \sqrt{(R^2 - R_H^2)} \qquad (1)$$

Here, R denotes an allowable resolution, $R_H$ denotes the highest resolution, $r_0$ denotes a diameter of a sphere on which the transducers 321 are arranged, and $\phi_d$ denotes a diameter of the transducer 321. Herein, the allowable resolution R is set to a half the highest resolution.

The moving system 34 is a three-axis moving system capable of performing a three-dimensional scan in the X, Y, and Z directions. The three-axis moving system includes, for example, a combination of a stage, a linear guide (not illustrated), a feed screw system (not illustrated), and a motor (not illustrated); and is configured to move the light radiation unit 31, the receiver 32, the camera 33, or the like.

The moving system 34 is configured to move the receiver 32 from a position at which the receiver 32 receives an acoustic wave from one examined portion held by one examined-portion holding member among two examined-portion holding members, to a position at which the receiver 32 receives an acoustic wave from another examined portion held by the other examined-portion holding member. In addition, in the case where the examined-portion information acquisition apparatus does not include the examined-portion holding members, the moving system 34 may be configured in the following manner. The moving system 34 is configured to move the receiver 32 from a position at which the receiver 32 receives an acoustic wave from one examined portion inserted into one opening among two openings provided in an examined-object supporting member, to a position at which the receiver 32 receives an acoustic wave from another examined portion inserted into the other opening.

The transducer 321 receives an acoustic wave and converts the acoustic wave into an electric signal which is an analog signal. Herein, a reception signal includes an analog signal output from each transducer 321 and a digital signal resulting from A/D conversion. Any type of transducer, such as a transducer using the piezoelectric effect, a transducer using resonance of light, or a transducer using a change in capacitance, such as a capacitive micromachined ultrasonic transducer (CMUT), may be used as long as the transducer is capable of detecting an acoustic wave. In this embodiment, the plurality of transducers 321 are arranged. By using such a multi-dimensional array of transducers, an acoustic wave can be received simultaneously at a plurality of positions and the time taken for reception can be shortened.

The supporting member 322 is a member that supports the plurality of transducers 321. The supporting member 322 preferably has a shape that enables arrangement of the plurality of transducers 321. That is, from the viewpoint of reception sensitivity to an acoustic wave, the supporting member 322 preferably supports the plurality of transducers 321 so that the plurality of transducers 321 are arranged on a closed curved surface that surrounds the examined portion (breast). For example, when the plurality of transducers 321 are arranged on a spherical surface so that directions (directivity axes) in which the plurality of transducers 321 have the highest reception sensitivities point toward the center of the sphere, a reception sensitivity of the receiver 32 toward the center becomes the highest. However, it is difficult to arrange the plurality of transducers 321 on the entire closed curved surface that surrounds the breast.

Accordingly, for example, the supporting member 322 may have a concave portion, and the plurality of transducers 321 may be arranged along a concave surface of the concave portion.

The concave surface may be a curved surface or may be composed of a plurality of flat surfaces. The concave surface may preferably be a curved surface (approximated curved surface in the case where the concave surface is composed of a plurality of flat surfaces) having a center of curvature located at the certain region (high-sensitivity region). Also, the curved surface preferably has a shape so that, in the case where the plurality of transducers 321 are arranged along the curved surface, directions in which at least some of the plurality of transducers have the highest reception sensitivities cross one another. Further, the concave surface preferably has a shape so that an angle between planes perpendicular to the directions in which adjacent transducers 321 among the plurality of transducers 321 have the highest reception sensitivities is larger than 0 degrees and smaller than 180 degrees.

Such a shape of the concave surface of the supporting member 322 causes the directions (directivity axes) in which the plurality of transducers 321 arranged on the supporting member 322 have the highest reception sensitivities to converge at a certain specific region. Thus, a reception sensitivity of the receiver 32 to an acoustic wave propagating from the certain region can be made higher.

Specifically, the supporting member 322 can have a spherical surface and the plurality of transducers 321 can be arranged along the spherical surface. Herein, the spherical surface encompasses spherical surfaces other than a surface of the complete sphere. That is, the spherical surface encompasses a spherical surface with an opening, such as a hemisphere surface. Also, the spherical surface encompasses a surface that has unevenness but can be considered as a spherical surface and a surface of an ellipsoid (shape obtained by expanding an ellipse in three dimension and its surface is composed of a quadric surface) that can be considered as a spherical surface.

The shape of the supporting member 322 preferably is a shape that allows directions in which the plurality of transducers 321 provided on the supporting member 322 have the highest reception sensitivities to point toward a certain region inside the examined portion. As described above, the certain region is a region for which a reception sensitivity of the receiver 32 to an acoustic wave propagating from the certain region becomes higher than that of the case where the plurality of transducers 321 are arranged in parallel with one another. In the case where the examined-portion information acquisition apparatus includes the examined-portion holding members, the shape of the supporting member 322 and arrangement of the plurality of transducers 321 are preferably set so that the certain region can be located within an examined-portion insertion region of the examined-portion holding member at the time of reception of an acoustic wave.

In addition, as in this embodiment, the plurality of transducers 321 are preferably arranged on the supporting member 322 so that reception surfaces of the plurality of transducers 321 are located on the inner side of the supporting member 322 having a hemisphere shape. Here, the hemisphere shape encompasses not only a shape obtained by accurately halving a sphere but also a shape obtained by removing a part of a sphere. Also, the sphere encompasses not only a complete sphere but also a surface that has unevenness but can be considered as a sphere and an ellipsoid (shape obtained by expanding an ellipse in three dimension and its surface is composed of a quadric surface) that can be considered as a spherical surface.

Also, how the plurality of transducers 321 are arranged on the supporting member 322 is preferably an arrangement that enables sampling at equal intervals in the k-space. Here, data in the k-space can be obtained by performing Fourier transform on data in the real space. That is, coordinates in the real space are position coordinates (x, y, z), whereas axes in the k-space (kx, ky, kz) are spatial frequencies. For example, the plurality of transducers 321 are preferably spirally arranged as described in Japanese Patent No. 4341987. Note that the supporting member 322 may have any given shape as long as the plurality of transducers 321 can be arranged thereon so that a desired high-resolution region can be formed.

Further, the light radiation unit 31 is preferably arranged on the supporting member 322. This keeps a relationship between an acoustic-wave reception position and a light radiation position constant, and enables more uniform photoacoustic wave information to be acquired. An allowed irradiated area of the breast is regulated by the standard of American National Standards Institute (ANSI). Accordingly, in order increase an amount of light that propagates to inside of the breast, it is preferable to increase a radiation intensity and a light radiation area; however, the light radiation area is limited from the viewpoint of the cost of the light source 5 or the like. Also, from the viewpoint of the directivities of the transducers 321, the use efficiency of the amount of light is low when light is radiated onto a region for which reception sensitivity is low. Therefore, it is not efficient to radiate light onto the entire breast. That is, because it is efficient to radiate light onto a region for which the receiver 32 has a high sensitivity, light is also desirably moved together with the receiver 32. For example, the examined-portion information acquisition apparatus may further include a light-radiation-unit moving system (not illustrated) configured to move the light radiation unit 31. The light-radiation-unit moving system is configured to change a position of the light radiation unit 31 when the receiver 32 receives an acoustic wave from a first examined portion (left breast) and a position of the light radiation unit 31 when the receiver 32 receives an acoustic wave from a second examined portion (right breast).

In FIG. 1, light radiated from the light source 5 is led to the examined object while being processed to have a desired light distribution shape by optical components such as a lens and a mirror. In addition, light radiated from the light source 5 may be propagated by using an optical fiber, an optical fiber bundle in which optical fibers are bundled, or an optical waveguide, such as an articulating arm including a barrel which includes a mirror and the like. These are also considered as the light guide 51. Other examples of the light guide 51 include a mirror that reflects light, a lens that condenses, enlarges, changes the shape of light, and a diffusing plate that diffuses light.

As these optical components, any given optical components can be used as long as light emitted from the light source 5 is radiated onto the breast in a desired shape. Note that instead of being condensed by a lens, light is preferably diffused to an area of certain extent because a region of the examined object for which an acoustic wave can be received is extended. Also, in the case where desired pulsed light can be radiated onto the breast directly from the light source 5, the examined-portion information acquisition apparatus need not include the light guide 51.

Figure 3:
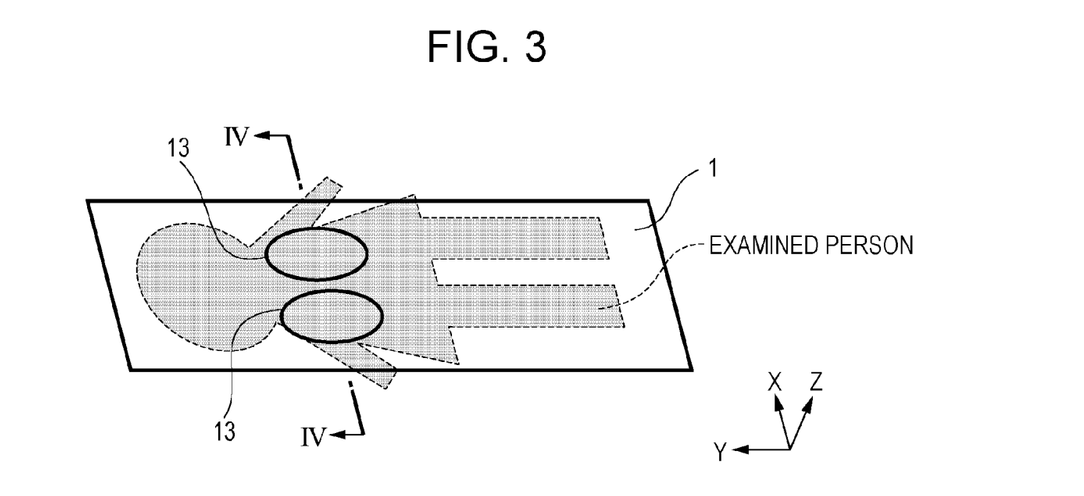
FIG. 3 is a conceptual diagram illustrating the position of an examined person when information concerning examined portions is acquired.

FIG. 3 is a conceptual diagram illustrating the position of an examined person when information concerning examined portions is acquired in this embodiment. The examined-portion information acquisition apparatus according to this exemplary embodiment is configured such that the bed 1 is provided with two openings (breast insertion openings) 13 which are examined-portion insertion portions so that right and left breasts can be inserted at the same time. Note that it is sufficient that the breast insertion openings 13 are configured so that both breasts can be inserted at the same time, and thus one large insertion opening may be provided. Although FIG. 3 illustrates an example in which the holding members 11 are not used, the holding members 11 may be inserted into the breast insertion openings 13 to support the breasts. In this case, the breasts are preferably supported by a breast holding member capable of supporting both breasts at the same time so that the breasts do not droop too low. The breast holding member may be constituted as one member, or may be constituted as different members for the right and left breasts.

Figure 4:
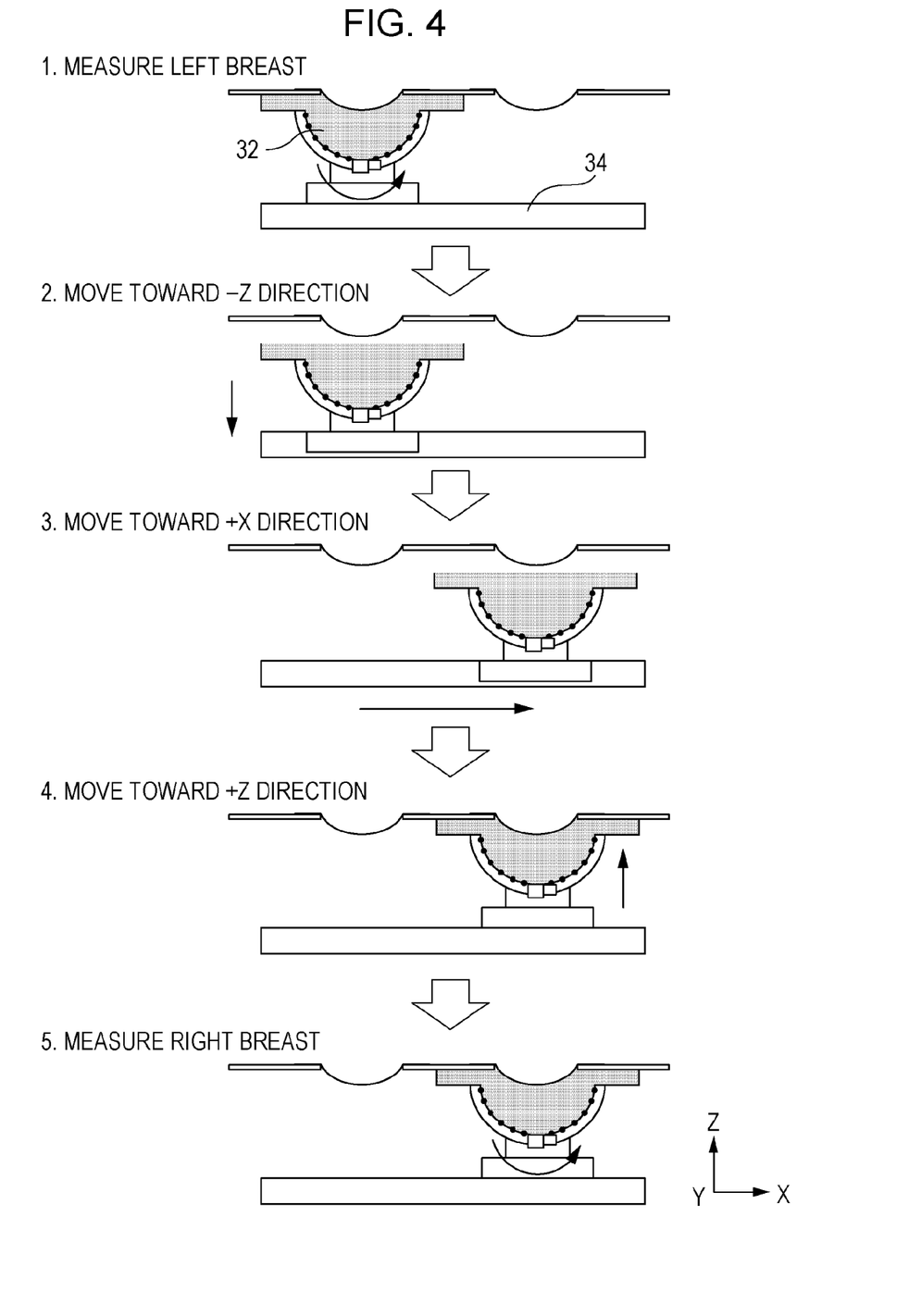
FIG. 4 is a conceptual diagram of the reception unit and a bed portion of the examined-portion information acquisition apparatus viewed at a cross-section taken along line IV-IV of FIG. 3.

A scan performed by the receiver 32 when acoustic waves from the right and left breasts are received will be described in detail using FIG. 4 and FIGS. 5A to 5C. FIG. 4 is a conceptual diagram of the reception unit 3 and the bed portion of the examined-portion information acquisition apparatus according to the embodiment of the present invention viewed at a cross-section taken along line IV-IV illustrated in FIG. 3.

First, a measurement is performed on the left breast of the examined person. The receiver 32 moves in a direction of a +Z direction component (e.g., +Z direction) from an acoustic-wave reception start position for the left breast. Here, the Z direction is a direction perpendicular to the X-Y plane which is a plane of a scan path taken by the receiver 32 when it receives an acoustic wave.

Next, the receiver 32 moves within a region on the X-Y plane that coincides with the left breast to receive an acoustic wave. For example, the receiver 32 receives an acoustic wave while moving in the X direction within a scan region of the receiver 32. Upon reaching the end of the scan region, the receiver 32 moves in the Y direction over a distance so that no gap is created between the scan region and the reception region of the receiver 32. Next, the receiver 32 receives an acoustic wave while moving along the X direction in a direction opposite to that of the previous X-direction scan. Upon reaching the end of the scan region, the receiver 32 again moves in the Y direction over a distance so that no gap is created between the scan region and the reception region of the receiver 32. The receiver 32 repeatedly performs the above-described process to receive an acoustic wave from the examined portion.

After finishing reception of an acoustic wave from the left breast, the receiver 32 moves in the −Z direction to avoid interference between the matching-agent container and the holding member 11 or the breast. Thereafter, the receiver 32 moves to an acoustic-wave reception start position for the right breast. Thereafter, the receiver 32 again moves in the +Z direction. Upon the position of the receiver 32 reaching a predetermined position in the Z direction, the receiver 32 starts reception of an acoustic wave from the right breast. Reception of an acoustic wave from the right breast can also be performed along a scan path similar to that adopted when an acoustic wave is received from the left breast. Alternatively, the scan path may be changed for the right and left breasts. Here, movement of the receiver 32 in the ±Z directions and movement of the receiver 32 to the acoustic-wave reception start position for the right breast may be performed at the same timing.

A sensor (not illustrated) detects the position of the receiver 32, and outputs information to a control unit 2. The control unit 2 includes a storage unit configured to store data of a scan path taken by the receiver 32, and a computing unit. The computing unit generates a signal for controlling a moving direction, a velocity, and the like of the receiver 32 from the output of the sensor and the data stored in the storage unit so that the receiver 32 moves along the predetermined scan path, and outputs the signal to the moving system 34. As the sensor, for example, a potentiometer using an encoder or a variable resistor, or a camera can be used. As the storage unit, a storage medium such as a read only memory (ROM), a random access memory (RAM), or a hard disk can be used. As the computing unit, a CPU, an FPGA chip, or the like can be used.

In this embodiment, the receiver 32 is moved to the acoustic-wave reception start positions for the right and left breasts by the moving system 34 included in the reception unit 3; however, the configuration is not limited to this one and the movement may be performed by using another moving system (not illustrated) configured to move the whole reception unit 3.

Figure 5A:
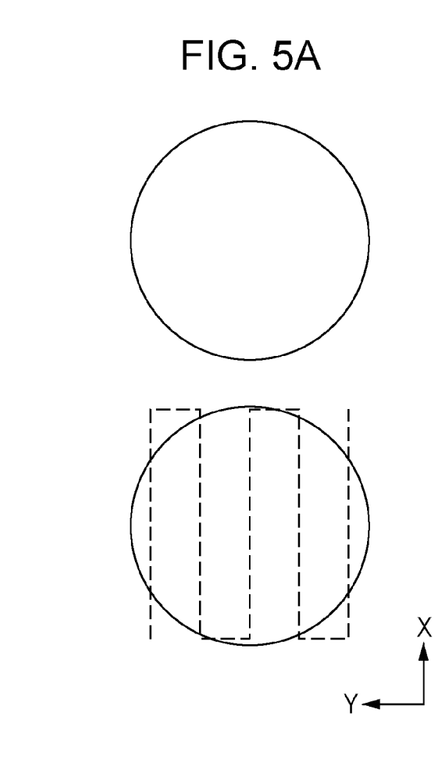
FIGS. 5A to 5C are conceptual diagrams illustrating an example of a scan path taken by a receiver.
Figure 5B:
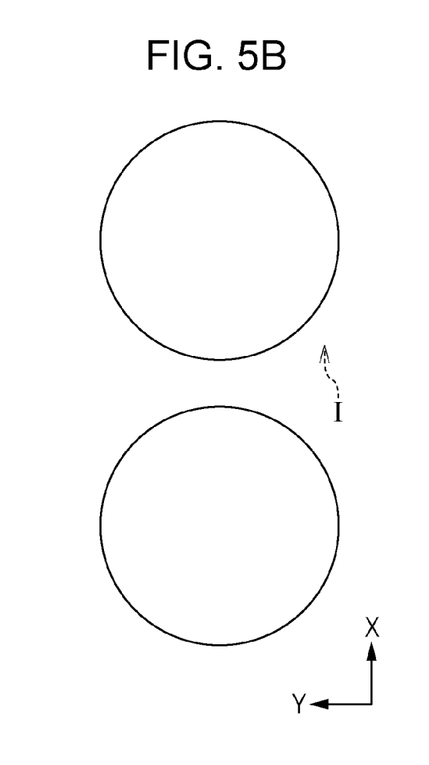
Figure 5C:
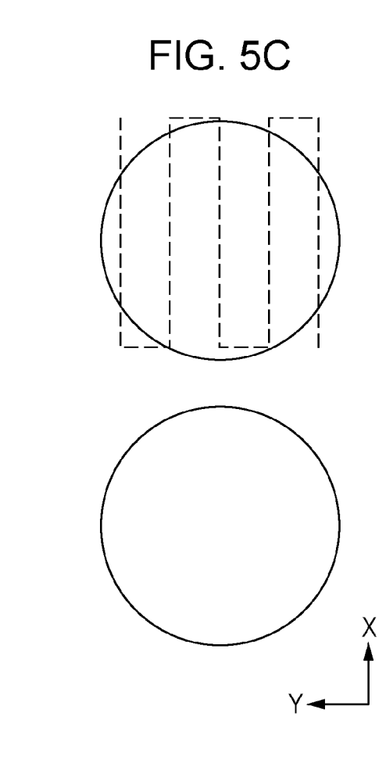

FIGS. 5A to 5C are conceptual diagrams illustrating the scan path taken by the receiver 32 on the X-Y plane in accordance with this embodiment. In FIGS. 5A and 5C, a dashed line represents a scan path taken by the receiver 32. Also, as indicated by a dashed-line arrow in FIG. 5B, the receiver 32 moves along a path (breast switching path) obtained by connecting a position at which the receiver 32 has finished reception of an acoustic wave from the left breast (left-breast reception end point) to a position at which the receiver 32 starts reception of an acoustic wave from the right breast (right-breast reception start point) as a straight line. Through such a movement, the receiver 32 can be moved in the shortest distance.

Also, the receiver 32 moves such that a scan path taken by the receiver 32 from a point immediately before reception from the first examined portion is finished to a point at which reception from the first examined portion is finished or a scan path taken by the receiver 32 from a point at which reception from the second examined portion is started to a point immediately after reception from the first examined portion is started becomes substantially in parallel with a scan path taken by the receiver 32 at the time of switching of reception from the examined portion. In this embodiment, finishing reception from the first examined position corresponds to finishing reception of an acoustic wave from the left breast, and finishing reception from the second examined portion corresponds to finishing reception of an acoustic wave from the right breast. Also, the path taken when an acoustic wave is received from an examined portion corresponds to a path taken when an acoustic wave is received from the left breast or the right breast, and the time of switching of reception from the examined portion corresponds to the time at which reception of an acoustic wave from the left breast is switched to reception of an acoustic wave from the right breast. By performing a scan in this manner, switching from reception of an acoustic wave from the left breast to reception of an acoustic wave from the right breast performed by the receiver 32 becomes smooth, and consequently vibration of the apparatus, especially, vibration of the bed 1, caused by a scan performed by the receiver 32 can be suppressed. Also, irregularities on the liquid surface of the matching agent 35 within the receiver 32 caused by a scan performed by the receiver 32 can be reduced. Consequently, a decrease in accuracy of the reception signal resulting from irregularities on the liquid surface of the matching agent 35 can be reduced.

Further, the moving system 34 is preferably controlled so that a change in a value obtained by differentiation of a scan velocity (moving velocity) of the receiver 32 by time, that is, a change in acceleration, is continuous during at least one of when reception from the left breast is performed, when reception from the right breast is performed, and when a movement is performed from a position at which reception from the left breast is finished to a position at which reception from the right breast is started. By performing a scan in this manner, vibration of the apparatus, especially, vibration of the bed 1, caused by a scan performed by the receiver 32 can be further suppressed. Also, irregularities on the liquid surface of the matching agent 35 within the receiver 32 caused by a scan performed by the receiver 32 can be reduced. Consequently, a decrease in accuracy of the reception signal resulting from irregularities on the liquid surface of the matching agent 35 can be reduced.

The above-described movement of the receiver 32 performed by the moving system 34 is controlled by the control unit 2. For example, the control unit 2 is configured to input, to the moving system 34, a signal for causing the moving system 34 to move the receiver 32 to a position at which the receiver 32 receives an acoustic wave from the left breast or the right breast. The control unit 2 is also configured to input, to the moving system 34, a signal for causing the moving system 34 to move the receiver 32 from a position at which the receiver 32 receives an acoustic wave from the left breast to a position at which the receiver 32 receives an acoustic wave from the right breast.

Further, the control unit 2 may be configured to input, to the moving system 34, a driving signal for causing the moving system 34 to linearly move the receiver 32 from a position at which the receiver 32 has finished reception of an acoustic wave from the left breast to a position at which the receiver 32 starts reception of an acoustic wave from the right breast. The control unit 2 may also be configured to input, to the moving system 34, a driving signal for causing the moving system 34 to move the receiver 32 in a direction of a perpendicular component to a plane of a scan path taken by the receiver 32 when the receiver 32 receives an acoustic wave from the left breast or the right breast (in the Z direction in this embodiment).

The control unit 2 may be configured to input, to the moving system 34, a driving signal for causing the moving system 34 to move the receiver 32 such that a straight line connecting the position at which the receiver 32 finishes reception of an acoustic wave from the left breast and a position at which the receiver 32 starts reception of an acoustic wave from the right breast is substantially in parallel with a direction in which the receiver 32 moves when starting reception of an acoustic wave from the right breast.

The control unit 2 may also be configured to input, to the moving system 34, a driving signal for causing the moving system 34 to move the receiver 32 such that a straight line connecting a position at which the receiver 32 finishes reception of an acoustic wave from the left breast and a position at which the receiver 32 starts reception of an acoustic wave from the right breast is substantially in parallel with a direction in which the receiver 32 moves when finishing reception of an acoustic wave from the left breast.

Further, the control unit 2 may be configured to input, to the moving system 34, a driving signal that makes a change in a value obtained by differentiation, by time, of a moving velocity of the receiver 32 continuous during at least one of when an acoustic wave from the left breast or the right breast is received and when the receiver 32 is moved from a position at which the receiver 32 finishes reception of an acoustic wave from the left breast to a position at which the receiver 32 starts reception of an acoustic wave from the right breast.

In this exemplary embodiment, the case of receiving acoustic waves in the order of the left breast and the right breast has been used as an example; however, similar advantages can be obtained also in the case where acoustic waves are received in the order of the right breast and the left breasts.

Note that the examined-portion information acquisition apparatus may include an adjustment system (not illustrated) configured to adjust the positions of the breast insertion openings 13 or the breast holding members (not illustrated) in accordance with the positions of the breasts of the examined person. The adjustment system may be electrically operated or manually operated by an operator. By adopting this configuration, a load imposed on the examined person can be reduced when the breasts are positioned.

Figure 6:
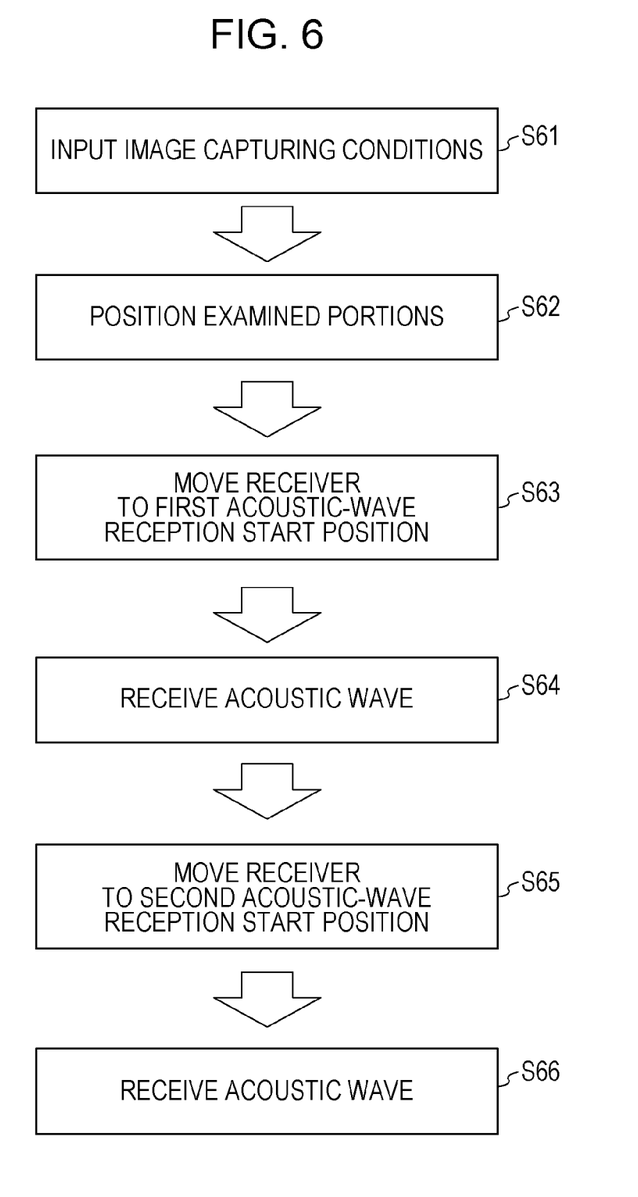
FIG. 6 is a diagram illustrating a flow of how information concerning examined portions is acquired.

FIG. 6 is a diagram illustrating a flow of how the examined-portion information acquisition apparatus according to this embodiment acquires information concerning examination portions. An operator installs the holding members 11 in accordance with the breasts subjected to image capturing, if necessary. The operator inputs image capturing conditions (S61). Here, the image capturing conditions include parameters related to reception of an acoustic wave, such as the acoustic-wave reception start positions, the size of the scan region, or a moving velocity (scan velocity) of the receiver 32. The image capturing conditions may be decided by the operator through a visual check. After the breasts which are examined portions have been positioned in the holding members 11 (S62), the receiver 32 moves to a first acoustic-wave reception start position (S63), and performs reception of an acoustic wave concerning a first examined portion (herein, the left breast) (S64). Next, the receiver 32 moves to a second acoustic-wave reception start position (S65), and performs reception of an acoustic wave concerning a second examined portion (herein, the right breast) (S66).

As described above, in accordance with one aspect of the present invention, the time taken to receive acoustic waves from examined portions can be shortened, and a load imposed on a subject person can be reduced in the case where the examined portions are of a living body.

Second Embodiment

In this embodiment, an example of an examined-portion information acquisition apparatus which has a scan path of the receiver 32 different from that of the first embodiment will be described. In this embodiment, the scan path at the position of the receiver 32 is circular. Because the other configurations and operations are similar to those of the examined-portion information acquisition apparatus according to the first embodiment, a description thereof is omitted.

A scan performed by the receiver 32 during reception from the right and left breasts will be described in detail using FIG. 4 and FIGS. 7A to 7C. FIG. 4 is a conceptual diagram of the reception unit 3 and the bed portion of the examined-portion information acquisition apparatus according to this embodiment of the present invention viewed at a cross-section taken along line IV-IV illustrated in FIG. 3.

First, a measurement is performed on the left breast of the examined person. The receiver 32 moves in the +Z direction from an acoustic-wave reception start position for the left breast. Next, the receiver 32 moves along a circular path on the X-Y plane to surround the left breast, and receives an acoustic wave. The X-Y plane is a plane of a scan path taken by the receiver 32 when the receiver 32 receives an acoustic wave. Then, the receiver 32 moves in the −Z direction to avoid interference between the matching-agent container and the holding member 11 or the breast, and moves to an acoustic-wave reception start position for the right breast. Thereafter, the receiver 32 again moves in the +Z direction. Upon the position of the receiver 32 reaching a predetermined position in the Z direction, the receiver 32 starts reception of an acoustic wave from the right breast. Reception of an acoustic wave from the right breast can be performed along a scan path similar to that used when an acoustic wave from the left breast is received. Alternatively, the scan path may be changed for the right and left breasts.

Here, movement in the ±Z directions and movement to the acoustic-wave reception start position for the right breast may be performed at the same timing.

In this embodiment, the receiver 32 is moved to the acoustic-wave reception start positions for the right and left breasts by the moving system 34 included in the reception unit 3; however, the configuration is not limited to this one and the movement may be performed by using another moving system (not illustrated) configured to move the whole reception unit 3.

Figure 7A:
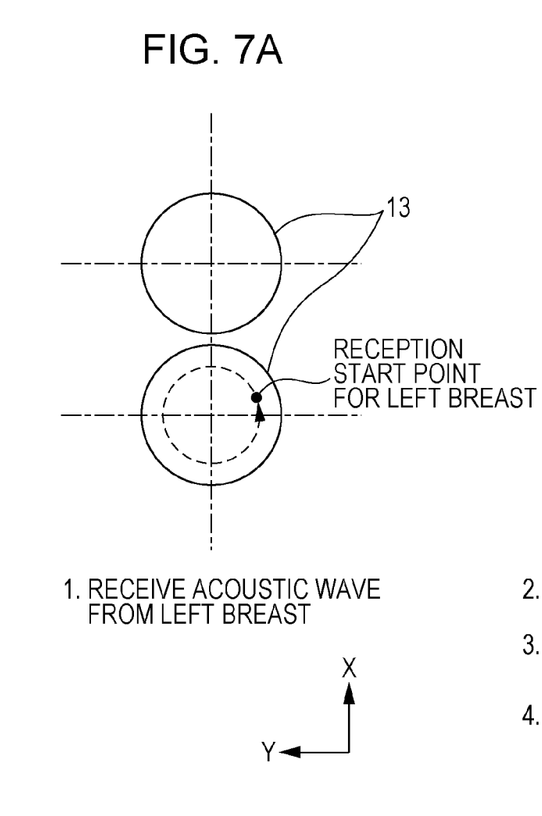
FIGS. 7A to 7C are conceptual diagrams illustrating an example of a scan path taken by the receiver.
Figure 7B:
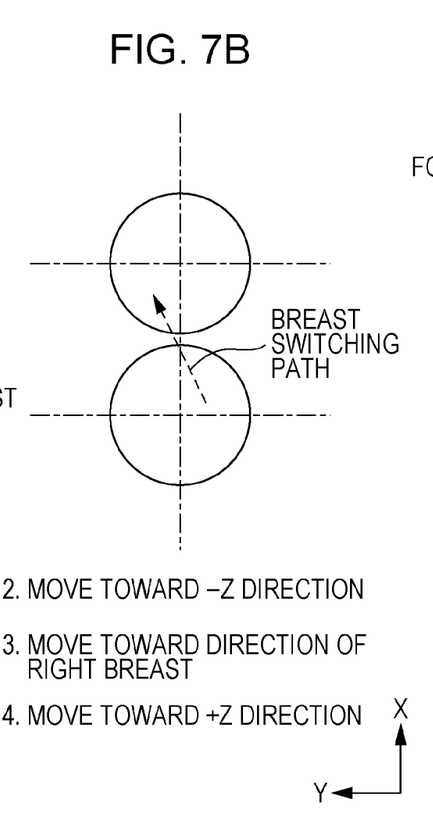
Figure 7C:
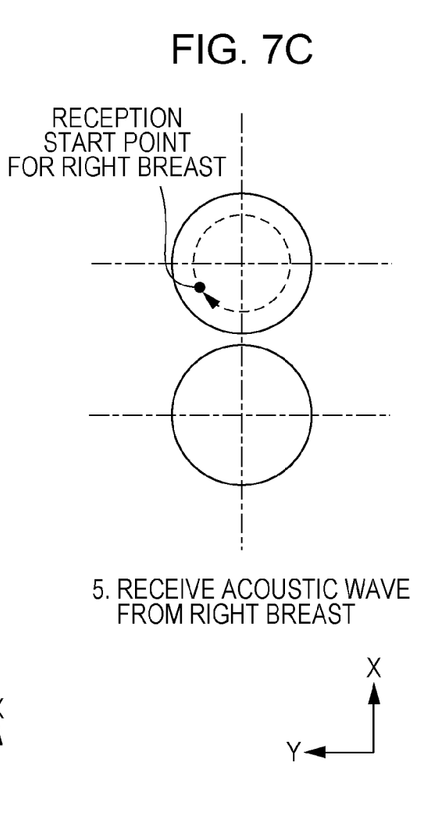

FIGS. 7A to 7C are conceptual diagrams illustrating a scan path taken by the receiver 32 on the X-Y plane in accordance with this embodiment of the present invention. A dashed line represents a scan path taken by the receiver 32. Between steps 2 and 4 of FIG. 4, the receiver 32 moves along a path (breast switching path) obtained by connecting a position at which the receiver 32 has finished reception of an acoustic wave from the left breast (left-breast reception end point) and a position at which the receiver 32 starts reception of an acoustic wave from the right breast (right-breast reception start point). Through such a movement, the receiver 32 can be moved in the shortest distance.

In addition, the receiver 32 can be moved such that directions of tangents of examined-portion acoustic-wave reception paths at a first-examined-portion reception end point and at a second-examined-portion reception start point are substantially in parallel with the breast switching path. In this embodiment, the first-examined-portion reception end point is a point at which reception of an acoustic wave from the left breast is finished, and the second-examined-portion reception start point is a point at which reception of an acoustic wave from the right breast is started. Also, the examined-portion acoustic-wave reception path is a path taken by the receiver 32 when an acoustic wave from the left breast or the right breast is received, and the breast switching path is a path taken by the receiver 32 when reception of an acoustic wave from the left breast is switched to reception of an acoustic wave from the right breast. By performing a scan in such a manner, an abrupt acceleration or deceleration of the receiver 32 can be suppressed, and consequently vibration of the apparatus, especially, vibration of the bed 1, caused by a scan performed by the receiver 32 can be suppressed. Also, irregularities on the liquid surface of the matching agent 35 within the receiver 32 caused by a scan performed by the receiver 32 can be reduced. Consequently, a decrease in accuracy of the reception signal resulting from irregularities on the liquid surface of the matching agent 35 can be reduced.

In addition, the moving system 34 is preferably controlled such that a change in a value obtained by differentiation of a scan velocity of the receiver 32 by time, that is, a change in acceleration is continuous when an acoustic wave from the left breast is received, when an acoustic wave from the right breast is received, and when the receiver 32 is moved from a position at which the receiver 32 has finished reception of an acoustic wave from the left breast to a position at which the receiver 32 starts reception of an acoustic wave from the right breast. By performing a scan in this manner, vibration of the apparatus, especially, vibration of the bed 1, caused by a scan performed by the receiver 32 can be further suppressed. Also, irregularities on the liquid surface of the matching agent 35 within the receiver 32 caused by a scan performed by the receiver 32 can be reduced. Consequently, a decrease in accuracy of the reception signal resulting from irregularities on the liquid surface of the matching agent 35 can be reduced.

In this exemplary embodiment, the case of receiving acoustic waves in the order of the left breast and the right breast has been used as an example; however, similar advantages can be obtained also in the case where acoustic waves are received in the order of the right breast and the left breasts.

Note that the examined-portion information acquisition apparatus may further include an adjustment system (not illustrated) configured to adjust the positions of the breast insertion openings 13 or the breast holding members (not illustrated) in accordance with the positions of the breasts of the examined person. The adjustment system may be electrically operated or manually operated by an operator. By adopting this configuration, a load imposed on the subject can be reduced when the breasts are positioned.

An example of a flow of how information concerning examined portions is acquired in this embodiment can be illustrated in FIG. 6 as in the first embodiment. The operator installs the holding members 11 in accordance with the breasts subjected to image capturing, and inputs image capturing conditions (S61). Here, the image capturing conditions include parameters related to reception of an acoustic wave, such as the maximum value of the coordinates r(t) in a radial direction and a moving velocity of the receiver 32. The image capturing conditions may be decided by the operator through a visual check. After the breasts which are examined portions have been positioned in the holding members 11 (S62), the receiver 32 moves to a first acoustic-wave reception start position (S63), and performs reception of an acoustic wave concerning a first examined portion (herein, the left breast) (S64). Next, the receiver 32 moves to a second acoustic-wave reception start position (S65), and performs reception of an acoustic wave concerning a second examined portion (herein, the right breast) (S66).

In this embodiment, a scan path at the position of the receiver 32 when an acoustic wave from the examined portion is received is circular. Accordingly, the receiver 32 can receive an acoustic wave from the examined portion without making the moving velocity of the receiver 32 zero or without inverting the sign of acceleration of the movement of the receiver 32 while performing reception. That is, the receiver 32 can be moved smoothly during reception.

At this time, by moving the receiver 32 from a position at which reception of an acoustic wave from one examined portion (the left breast in this embodiment) is finished to a position at which reception of an acoustic wave from another examined portion (the right breast in this embodiment) is started along the above-described path or at the above-described value obtained by differentiation of the moving velocity by time, a smooth movement can be maintained.

Therefore, an abrupt acceleration or deceleration of the receiver 32 is suppressed, and consequently vibration of the apparatus, especially, vibration of the bed 1, caused by a scan performed by the receiver 32 can be suppressed more effectively. Also, irregularities on the liquid surface of the matching agent 35 within the receiver 32 caused by a scan performed by the receiver 32 can be reduced more effectively.

Consequently, a decrease in accuracy of the reception signal resulting from irregularities on the liquid surface of the matching agent 35 can be reduced more effectively.

The above-described movement of the receiver 32 performed by the moving system 34 is controlled by the control unit 2. The control unit 2 is configured to input, to the moving system 34, driving signals similar to those used in the first embodiment. The control unit 2 may also be configured to input, to the moving system 34, a driving system for causing the moving system 34 to move the receiver 32 so that the sign of acceleration of movement is not inverted while an acoustic wave is received from the left breast or the right breast.

Third Embodiment

In this embodiment, an example of an examined-portion information acquisition apparatus which has a path at the position of the receiver 32 different from those of the first and second embodiments will be described. In this embodiment, a scan path at the position of the receiver 32 is a spiral path (spiral pattern). Because configurations other than the scan path taken by the receiver 32 during reception of an acoustic wave from an examined portion are similar to those of the first or second embodiment, only the scan path taken by the receiver 32 will be described in this embodiment.

Figure 8:
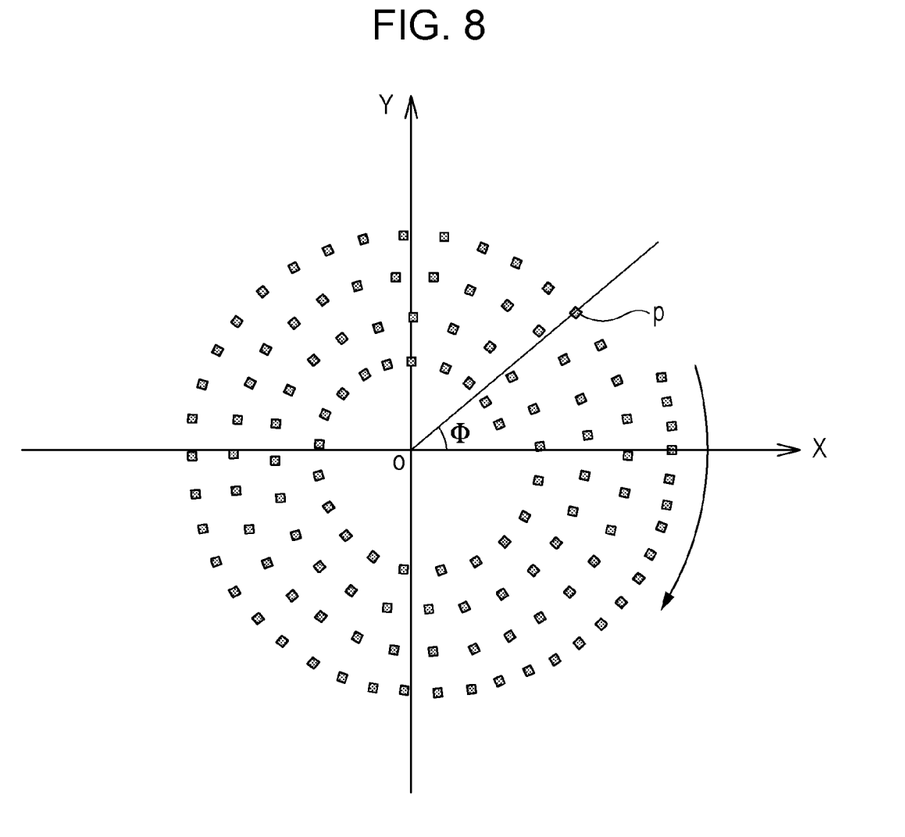
FIG. 8 is a conceptual diagram illustrating an example of a scan path taken by the receiver.

The spiral path is a scan path that enables a movement in which coordinates in a radial direction relative to the rotation center changes to increase or decrease. FIG. 8 is a conceptual diagram illustrating an example of the scan path of the receiver 32 in accordance with this embodiment, and a diagram that schematically illustrates an example of a movement along the spiral path. A point o in FIG. 8 represents the center of the scan path taken by the receiver 32, whereas black dots represent positions of the receiver 32 at different time points during reception of an acoustic wave. The receiver 32 moves along the positions of the black dots. A point p represents one point along the scan path taken by the receiver 32. Coordinates (x, y) of the position of the point p in the polar coordinate system can be expressed as Expression (2).

$$x = r(t)\cos \Phi$$

$$y = r(t)\sin \Phi \qquad \text{(Expression 2)}$$

Here, r(t) represents coordinates (radius of movement) in the radial direction, and $\Phi$ represents an angle between the X axis and a line extending from the origin toward the point p. In this embodiment, the receiver 32 is moved such that the coordinates: r(t) in the radial direction on the scan path of the receiver 32 changes to increase or decrease. Further, the moving system 34 may move the receiver 32 such that a velocity in the tangent direction of the scan path is constant. In general, a timing at which an acoustic wave is received is decided by a repetition frequency of pulsed light emitted from the light source 5. For example, when a light source having a repetition frequency of 10 Hz is used, an acoustic wave can be produced once every 0.1 second. Accordingly, in the case where the velocity in the tangent direction is constant, sampling can be performed evenly in terms of the space when it is assumed that an acoustic wave is received at intervals of 0.1 second.

In addition, the moving system 34 preferably moves the receiver 32 from an outer side of the movement plane taking into account acceleration toward the origin. Specifically, if acceleration at an initial stage of movement is large, vibration of the whole apparatus becomes large and this vibration may influence the measurement. Thus, vibration of the apparatus can be reduced in the case where movement is started from an outer radius at which acceleration toward the origin is small and is performed toward an inner radius.

In addition, the moving system 34 preferably performs continuous movement for continuously moving the receiver 32 instead of step-and-repeat movement in which a movement and a stop are repeated. With this configuration, the time taken for movement can be reduced, and a load imposed on the examined person can be decreased. Also, because a change in acceleration of movement is small, the influence of vibration of the apparatus can be decreased.

The scan path at the position of the receiver 32 during reception of an acoustic wave from an examined portion in this embodiment is a spiral pattern. Accordingly, the receiver 32 can receive an acoustic wave from the examined portion without making the moving velocity of the receiver 32 zero or without inverting the sign of acceleration of movement of the receiver 32 during reception. That is, the receiver 32 can be moved smoothly during reception.

At this time, by moving the receiver 32 from a position at which reception of an acoustic wave from one examined portion (the left breast in this embodiment) is finished to a position at which reception of an acoustic wave from another examined portion (the right breast in this embodiment) is started along the above-described path or at the above-described value obtained by differentiation of the moving velocity by time, a smooth movement can be maintained.

Therefore, an abrupt acceleration or deceleration of the receiver 32 is suppressed, and consequently vibration of the apparatus, especially, vibration of the bed 1, caused by a scan performed by the receiver 32 can be suppressed more effectively. Also, irregularities on the liquid surface of the matching agent 35 within the receiver 32 caused by a scan performed by the receiver 32 can be reduced more effectively.

Consequently, a decrease in accuracy of the reception signal resulting from irregularities on the liquid surface of the matching agent 35 can be reduced more effectively.

The above-described movement of the receiver 32 performed by the moving system 34 is controlled by the control unit 2. The control unit 2 is configured to input, to the moving system 34, driving signals similar to those used in the second embodiment.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of U.S. Provisional Application No. 61/898,075, filed Oct. 31, 2013 which is hereby incorporated by reference herein in its entirety.

What is claimed is:

1. An examined-portion information acquisition apparatus comprising:
a plurality of examined-portion holding members each configured to hold a respective examined portion of an object;
the plurality of examined-portion holding members comprising:
a first examined-portion holding member configured to hold a first examined portion of the object;
a second examined-portion holding member configured to hold a second examined portion of the object;
a receiver configured to receive an acoustic wave; and
a moving system configured to move the receiver from a position at which the receiver receives an acoustic wave from the first examined portion held by the first examined-portion holding member to a position at which the receiver receives an acoustic wave from the second examined portion held by the second examined-portion holding member, wherein
the receiver includes:
a plurality of transducers each configured to receive an acoustic wave, and
a supporting member on which the plurality of transducers are arranged, and
the plurality of transducers are arranged on the supporting member such that directivity axes of some transducers among the plurality of transducers converge.

2. The examined-portion information acquisition apparatus according to claim 1, further comprising a controller configured to
input, to the moving system, a signal for causing the moving system to move the receiver so that the receiver receives an acoustic wave from the first examined portion,
input, to the moving system, a signal for causing the moving system to move the receiver from the position at which the receiver receives an acoustic wave from the first examined portion to the position at which the receiver receives an acoustic wave from the second examined portion, and
input, to the moving system, a signal for causing the moving system to move the receiver so that the receiver receives an acoustic wave from the second examined portion.

3. The examined-portion information acquisition apparatus according to claim 2, wherein the controller is further configured to input, to the moving system, a signal for causing the moving system to linearly move the receiver from a position at which the receiver has finished reception of an acoustic wave from the first examined portion to a position at which the receiver starts reception of an acoustic wave from the second examined portion.

4. The examined-portion information acquisition apparatus according to claim 2, wherein the controller is further configured to input, to the moving system, a signal for causing the moving system to move the receiver in a direction of a perpendicular component to a plane of a scan path taken by the receiver when the receiver receives an acoustic wave from the first examined portion or a plane of a scan path taken by the receiver when the receiver receives an acoustic wave from the second examined portion.

5. The examined-portion information acquisition apparatus according to claim 4, wherein the direction of the perpendicular component is vertical.

6. The examined-portion information acquisition apparatus according to claim 2, wherein a change in a value obtained by differentiation, by time, of a moving velocity of the receiver is continuous during at least one of when the receiver receives an acoustic wave from the first examined portion, when the receiver receives an acoustic wave from the second examined portion, and when the receiver is moved from a position at which the receiver has finished reception of an acoustic wave from the first examined portion to a position at which the receiver starts reception of an acoustic wave from the second examined portion.

7. The examined-portion information acquisition apparatus according to claim 2, wherein a straight line connecting a position at which the receiver has finished reception of an acoustic wave from the first examined portion and a position at which the receiver starts reception of an acoustic wave from the second examined portion is substantially in parallel with a direction in which the receiver moves when starting reception of an acoustic wave from the second examined portion.

8. The examined-portion information acquisition apparatus according to claim 2, wherein a straight line connecting a position at which the receiver has finished reception of an acoustic wave from the first examined portion and a position at which the receiver starts reception of an acoustic wave from the second examined portion is substantially in parallel with a direction in which the receiver moves when finishing reception of an acoustic wave from the first examined portion.

9. The examined-portion information acquisition apparatus according to claim 1, further comprising
a light source configured to generate light, wherein light from the light source is radiated from a light radiation unit.

10. The examined-portion information acquisition apparatus according to claim 1, further comprising:
   a light radiation unit configured to radiate light onto an examined object; and
   a light-radiation-unit moving system configured to move the light radiation unit, wherein
   the light-radiation-unit moving system is configured to change a position of the light radiation unit when the receiver performs reception of an acoustic wave from the one first examined portion and a position of the light radiation unit when the receiver performs reception of an acoustic wave from the second examined portion.

11. The examined-portion information acquisition apparatus according to claim 9, wherein light generated by the light source is near-infrared light.

12. An examined-portion information acquisition apparatus, comprising:
   an examined-object supporting member including a plurality of openings into each of which an examined portion of an object is inserted;
   the plurality of opening comprising:
      a first opening in which the first examined portion of the object is inserted;
      a second opening in which the second examined portion of the object is inserted;
   a receiver configured to receive an acoustic wave; and
   a moving system configured to move the receiver from a position at which the receiver receives an acoustic wave from the first examined portion inserted into the first opening among to a position at which the receiver receives an acoustic wave from the second examined portion inserted into the second opening, wherein
   the receiver includes:
      a plurality of transducers each configured to receive an acoustic wave, and
      a supporting member on which the plurality of transducers are arranged, and
   the plurality of transducers are arranged on the supporting member such that directivity axes of some transducers among the plurality of transducers converge.

13. The examined-portion information acquisition apparatus according to claim 12, further comprising a controller configured to
   input, to the moving system, a signal for causing the moving system to move the receiver so that the receiver receives an acoustic wave from the first examined portion,
   input, to the moving system, a signal for causing the moving system to move the receiver from the position at which the receiver receives an acoustic wave from the first examined portion to the position at which the receiver receives an acoustic wave from the second examined portion, and
   input, to the moving system, a signal for causing the moving system to move the receiver so that the receiver receives an acoustic wave from the second examined portion.

14. The examined-portion information acquisition apparatus according to claim 13, wherein the controller is further configured to input, to the moving system, a signal for causing the moving system to linearly move the receiver from a position at which the receiver has finished reception of an acoustic wave from the first examined portion to a position at which the receiver starts reception of an acoustic wave from the second examined portion.

15. The examined-portion information acquisition apparatus according to claim 13, wherein the controller is further configured to input, to the moving system, a signal for causing the moving system to move the receiver in a direction of a perpendicular component to a plane of a scan path taken by the receiver when the receiver receives an acoustic wave from the first examined portion or a plane of a scan path taken by the receiver when the receiver receives an acoustic wave from the second examined portion.

16. The examined-portion information acquisition apparatus according to claim 15, wherein the direction of the perpendicular component is vertical.

17. The examined-portion information acquisition apparatus according to claim 13, wherein a change in a value obtained by differentiation, by time, of a moving velocity of the receiver is continuous during at least one of when the receiver receives an acoustic wave from the first examined portion, when the receiver receives an acoustic wave from the second examined portion, and when the receiver is moved from a position at which the receiver has finished reception of an acoustic wave from the first examined portion to a position at which the receiver starts reception of an acoustic wave from the second examined portion.

18. The examined-portion information acquisition apparatus according to claim 13, wherein a straight line connecting a position at which the receiver has finished reception of an acoustic wave from the first examined portion and a position at which the receiver starts reception of an acoustic wave from the second examined portion is substantially in parallel with a direction in which the receiver moves when starting reception of an acoustic wave from the second examined portion.

19. The examined-portion information acquisition apparatus according to claim 13, wherein a straight line connecting a position at which the receiver has finished reception of an acoustic wave from the first examined portion and a position at which the receiver starts reception of an acoustic wave from the second examined portion is substantially in parallel with a direction in which the receiver moves when finishing reception of an acoustic wave from the first examined portion.

20. The examined-portion information acquisition apparatus according to claim 13, further comprising,
   a light source configured to generate light, wherein
   light from the light source is radiated from a light radiation unit.

21. The examined-portion information acquisition apparatus according to claim 13, further comprising:
   a light radiation unit configured to radiate light onto an examined object; and
   a light-radiation-unit moving system configured to move the light radiation unit, wherein
   the light-radiation-unit moving system is configured to change a position of the light radiation unit when the receiver performs reception of an acoustic wave from the first examined portion and a position of the light radiation unit when the receiver performs reception of an acoustic wave from the second examined portion.

22. The examined-portion information acquisition apparatus according to claim 20, wherein light generated by the light source is near-infrared light.

* * * * *